United States Patent [19]

Ansmann et al.

[11] Patent Number: 5,736,581
[45] Date of Patent: Apr. 7, 1998

[54] POLYGLYCEROL POLYRICINOLEATES

[75] Inventors: Achim Ansmann, Erkrath; Rolf Kawa, Monheim; Helga Gondek; Gabriele Strauss, both of Duesseldorf; Rainer Von Kries, Iltertissen, all of Germany

[73] Assignee: Henkel Kommanditgesellschaft auf Aktien, Duesseldorf, Germany

[21] Appl. No.: 718,449

[22] PCT Filed: Sep. 23, 1996

[86] PCT No.: PCT/EP95/00915

§ 371 Date: Sep. 23, 1996

§ 102(e) Date: Sep. 23, 1996

[87] PCT Pub. No.: WO95/25502

PCT Pub. Date: Sep. 28, 1995

[30] Foreign Application Priority Data

Mar. 21, 1994 [DE] Germany .................. 44 09 569.4

[51] Int. Cl.⁶ .................. A61K 7/48; A61K 47/14
[52] U.S. Cl. .................. 514/785; 424/401; 514/786; 514/937; 514/938; 514/939; 528/272; 528/306
[58] Field of Search .................. 424/401; 514/785, 514/786, 937, 938, 939; 528/272, 306

[56] References Cited

U.S. PATENT DOCUMENTS

| | | |
|---|---|---|
| 4,988,456 | 1/1991 | Takahashi et al. .................. 252/314 |
| 5,147,644 | 9/1992 | Oppenlaender et al. .................. 424/401 |
| 5,391,321 | 2/1995 | Grüning .................. 252/309 |

FOREIGN PATENT DOCUMENTS

| | | |
|---|---|---|
| 174 377 | 3/1986 | European Pat. Off. . |
| 440 203 | 8/1991 | European Pat. Off. . |
| 559 013 | 9/1993 | European Pat. Off. . |
| 579 159 | 1/1994 | European Pat. Off. . |
| 40 05 819 | 8/1991 | Germany . |
| 40 29 323 | 3/1992 | Germany . |
| 41 17 033 | 11/1992 | Germany . |
| 58 198 243 | 11/1983 | Japan . |
| WO 85/04346 | 10/1985 | Japan . |
| 1 187 051 | 7/1989 | Japan . |

OTHER PUBLICATIONS

"Kosmetische Faerbemittel" of the Farbstoffkommission der Deutschen Forschungsgemeinschaft, Verlag Chemie, Weinheim, 1984, pp. 81–106.

Primary Examiner—John M. Cooney, Jr.
Attorney, Agent, or Firm—Wayne C. Jaeschke; John E. Drach; Steven J. Trzaska

[57] ABSTRACT

Disclosed are novel polyglycerine polyricinoleates as emulsifiers obtained by the esterification of polyricinoleic acid with a natural condensation rate of from 2 to 10 with a polyglycerine mixture comprising 5–35 wt. % glycerine, 15–40 wt. % diglycerines, 10–30 wt. % triglycerines, 8–20 wt. % tetraglycerines, and 3–10 wt. % pentaglycerines, and the remainder being oligoglycerines. The materials have improved emulsifying capacity.

3 Claims, No Drawings

POLYGLYCEROL POLYRICINOLEATES

BACKGROUND OF THE INVENTION

1. Field of the Invention

This invention relates to new polyglycerol polyricinoleates obtainable by esterification of polyricinoleic acid with technical polyglycerol having a certain composition, to a process for their production, to formulations containing these substances and to the use of the new polyglycerol polyricinoleates as w/o emulsifiers.

2. Statement of Related Art

Polyglycerol polyricinoleates have long been known as w/o emulsifiers and may be used for the formulation of low-viscosity w/o emulsions [cf. EP-A1 0559013 (Th. Goldschmidt), EP-A1 044203 (Lotte Co.) and WO 85/04346 (Meiji Milk Prods.)]. However, it has been found that commercial polyglycerol polyricinoleates do not form emulsions with all the oils typically used in cosmetics, but only with those having a certain polarity range. In addition, these emulsions show only limited stability in storage.

Now, the problem addressed by the present invention was to provide new w/o emulsifiers which would form low-viscosity and storage-stable emulsions with a broad range of oils.

DESCRIPTION OF THE INVENTION

The present invention relates to polyglycerol polyricinoleates obtained by esterifying polyricinoleic acid having a degree of autocondensation of 2 to 10 with a polyglycerol mixture of the following composition:

| | |
|---|---|
| glycerol: | 5 to 35 (25 to 25) % by weight |
| diglycerols: | 15 to 40 (20 to 32) % by weight |
| triglycerols: | 10 to 35 (15 to 25) % by weight |
| tetraglycerols: | 8 to 20 (10 to 18) % by weight |
| pentaglycerols: | 3 to 10 (5 to 9) % by weight |
| oligoglycerols: | to 100 % by weight |

(the figures in brackets represent preferred ranges) by methods known per se.

It has surprisingly been found that the composition of the polyglycerol component has a critical bearing on the performance properties of the emulsifiers. The invention includes the observation that polyglycerol polyricinoleates containing less than 5% by weight or more than 35% by weight of glycerol in their polyglycerol component have significantly poorer emulsifying power.

The present invention also relates to a process for the production of polyglycerol polyricinoleates, in which polyricinoleic acid having a degree of autocondensation of 2 to 10 is esterified with a polyglycerol mixture of the following composition:

| | |
|---|---|
| glycerol: | 5 to 35 (25 to 25) % by weight |
| diglycerols: | 15 to 40 (20 to 32) % by weight |
| triglycerols: | 10 to 35 (15 to 25) % by weight |
| tetraglycerols: | 8 to 20 (10 to 18) % by weight |
| pentaglycerols: | 3 to 10 (5 to 9) % by weight |
| oligoglycerols: | to 100 % by weight |

(the figures in brackets represent preferred ranges) by methods known per se.

Production of the polyqlycerol polyricinoleates

The polyglycerol polyricinoleates may be produced in known manner. Preferably, the polyglycerol is prepared in a first step and the polyricinoleic acid in a second step and, finally, the two are condensed.

The preparation of a polyglycerol having the composition shown above may be carried out by autocondensation of glycerol in the presence of suitable catalysts, for example silicates according to DE-A1 4029323 (Henkel) or borates according to DE-A1 4117033 (Henkel), at temperatures in the range from 200° to 260° C.

The polyricinoleic acid is prepared, for example, by controlled thermal polycondensation of castor oil fatty acid of which around 90% by weight consists of ricinoleic acid. Linear esterification products containing 2 to 10 and, more particularly, 4 to 6 fatty acid units are preferably formed.

A complex mixture of homologous polyesters is formed in the subsequent condensation of the technical polyglycerol with the polyricinoleic acid. The percentage contents of mono-, di-, tri- and oligoesters in the polyglycerol polyricinoleates according to the invention are determined by the ratios in which the starting compounds are used. In one preferred embodiment of the process according to the invention, a polyglycerol polyricinoleate with particularly favorable performance properties is obtained by subjecting around 1000 kg of castor oil fatty acid to autocondensation until a product with an acid value of 50 to 55 is obtained and the product thus obtained is then further condensed with around 150 kg of technical polyglycerol having the composition shown above until the acid value has fallen to below 2.

Cosmetic and Pharmaceutical Formulations

The present invention also relates to cosmetic and/or pharmaceutical formulations containing the new polyglycerol polyricinoleates.

Suitable auxiliaries and additives are oils, co-emulsifiers, fats and waxes, stabilizers, thickeners, biogenic agents, film formers, fragrances, dyes, pearlescers, preservatives, UV filters, pigments, electrolytes (for example magnesium sulfate) and pH regulators.

Suitable oil components are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{10-18}$ fatty alcohols, esters of linear $C_{10-18}$ fatty acids with branched alcohols, more particularly 2-ethylhexanol, esters of linear and/or branched fatty acids with dihydric alcohols and/or Guerbet alcohols, triglycerides based on $C_{6-10}$ fatty acids, vegetable oils, branched primary alcohols, substituted cyclohexanes, Guerbet carbonates and/or dialkyl ethers. Of particular importance in this regard is the fact that the polyglycerol polyricinoleates according to the invention are suitable for the formation of emulsions using both polar and medium-polar to nonpolar oils with dipole moments in a range from <1 to >5 Debye.

Suitable co-emulsifiers are preferably known w/o and also o/w emulsifiers such as, for example, polyglycerol esters, sorbitan esters or partly esterified glycerides. Typical examples of fats are glycerides while suitable waxes include inter alia beeswax, paraffin wax or microwaxes, optionally in combination with hydrophilic waxes. Suitable stabilizers are metal salts of fatty acids such as, for example, magnesium, aluminium and/or zinc stearate. Suitable thickeners are, for example, crosslinked polyacrylic acids and derivatives thereof, polysaccharides, more particularly xanthan gum, guar guar, agar agar, alginates and tyloses, carboxymethyl cellulose and hydroxyethyl cellulose, fatty alcohols, monoglycerides and fatty acids, polyacrylates, polyvinyl alcohol and polyvinyl pyrrolidone. In the context of the invention, biogenic agents are, for example, plant extracts, protein hydrolyzates and vitamin complexes. Typical film formers are, for example, hydrocolloids, such as chitosan, polyvinyl pyrrolidone, vinyl pyrrolidone/vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearlescers are, for example, glycol distearic acid esters, such as ethylene glycol distearate, and also fatty acids and fatty acid monoglycol esters. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total percentage content of auxiliaries and additives may be 1 to 80% by weight and is preferably 5 to 40% by weight, based on the formulation, while the non-aqueous component ("active substance") makes up 20 to 80% by weight and preferably 30 to 70% by weight of the formulation. The formulations may be produced in known manner, i.e. for example by hot, cold, hot-hot/cold or PIT emulsification. These are purely mechanical processes which do not involve a chemical reaction.

Commercial Applications

The polyglycerol polyricinoleates according to the invention are distinguished by improved emulsifying power. The resulting emulsions are preferably low in viscosity and have higher stability in storage and, in particular, thermal stability by comparison with known products.

Accordingly, the present invention also relates to the use of the polyglycerol polyricinoleates according to the invention as w/o emulsifiers for the production of cosmetic and/or pharmaceutical formulations, for example skin cremes, body lotions, sunscreens and the like, in which they may be present in concentrations of 1 to 30% by weight and preferably 2 to 10% by weight, based on the particular formulation.

EXAMPLES

I. Polyqlycerol polyricinoleates used

The composition of the polyglycerol component is shown in Table 1.

The emulsifiers had a degree of condensation of 5 through their polyricinoleic acid component.

TABLE 1

| Composition of polyglycerol polyricinoleates | | |
|---|---|---|
| | Emulsifier A % by weight | Emulsifier B % by weight |
| Glycerol | 20 | 0 |
| Diglycerols | 30 | 21 |
| Triglycerols | 20 | 22 |
| Tetraglycerols | 15 | 20 |
| Pentaglycerols | 5 | 11 |
| Oligoglycerols | 10 | 26 |

Emulsifier A corresponds to the invention while emulsifier B is a commercial product intended for comparison.

II Performance Tests

The properties of emulsifiers A and B were tested in various w/o emulsions according to Tables 2a and 2b. Formulations F1 to F4 correspond to the invention while formulations F5 to F8 are intended for comparison. Myritol® 318 is a $C_{8-10}$ triglyceride, Cetiol® V is decyl oleate and Cetiol® SN is cetearyl isononanoate. The viscosity of the products was determined after storage (1 day and 1 week) using a Brookfield RVF viscosimeter (spindle 5, 10 r.p.m., 23° C.). The results are set out in Table 3 below.

TABLE 2a

| Formulations according to the invention | | | | |
|---|---|---|---|---|
| | F1 % | F2 % | F3 % | F4 % |
| Emulsifier A | 7.0 | 7.0 | 7.0 | 7.0 |
| Paraffin oil, low-viscosity | 20.0 | — | — | — |
| Myritol 318 | — | 20.0 | — | — |
| Cetiol V | — | — | 20.0 | — |
| Cetiol SN | — | — | — | 20.0 |
| Glycerol, 86% by weight | 5.0 | 5.0 | 5.0 | 5.0 |
| $MgSO_4.7H_2O$ | 0.5 | 0.5 | 0.5 | 0.5 |
| Formaldehyde | 0.1 | 0.1 | 0.1 | 0.1 |
| Water | To 100% | | | |

TABLE 2b

| Comparison formulations | | | | |
|---|---|---|---|---|
| | F5 % | F6 % | F7 % | F8 % |
| Emulsifier B | 7.0 | 7.0 | 7.0 | 7.0 |
| Paraffin oil, low-viscosity | 20.0 | — | — | — |
| Myritol 318 | — | 20.0 | — | — |
| Cetiol V | — | — | 20.0 | — |
| Cetiol SN | — | — | — | 20.0 |
| Glycerol, 86% by weight | 5.0 | 5.0 | 5.0 | 5.0 |
| $MgSO_4.7H_2O$ | 0.5 | 0.5 | 0.5 | 0.5 |
| Formaldehyde | 0.1 | 0.1 | 0.1 | 0.1 |
| Water | To 100% | | | |

TABLE 3

| Performance results | | | |
|---|---|---|---|
| Viscosity [mPas · s] | | | |
| Formulation | After 1 d | After 1 w | Remarks |
| F1 | 24800 | 24000 | Stable emulsions even after storage for more than 1 week |
| F2 | 22800 | 22000 | |
| F3 | 16000 | 15200 | |
| F4 | 30000 | 29000 | |
| F5 | — | — | No emulsion formed |
| F6 | — | — | Separates after 1 d |
| F7 | 16000 | 19000 | Unstable emulsion |
| F8 | — | — | Separates after 1 d |

The Examples show that stable and low-viscosity w/o emulsions are only reliably obtained, i,e. over a broad range of oils to be emulsified, where the polyglycerol polyricinoleates according to the invention are used.

What is claimed is:

1. A polyglycerol polyricinoleate made by the process which comprises reacting polyricinoleic acid having a degree of autocondensation of 2 to 10 with a polyglycerol mixture comprised of: (a) from about 5 to about 35% by weight of glycerol, (b) from about 15 to about 40% by weight of diglycerol,. (c) from about 10 to about 30% by weight of triglycerol, (d) from about 8 to about 20% by weight tetraglycerol, (e) from about 3 to 10% by weight pentaglycerol and, (f) the remainder oligoglycerol.

2. A process for producing a polyglycerol polyricinoleate which comprises reacting polyricinoleic acid having a degree of autocondensation of 2 to 10 with a polyglycerol mixture comprised of: (a) from about 5 to about 35% by weight of glycerol, (b) from about 15 to about 40% by weight of diglycerol, (c) from about 10 to about 30% by weight of triglycerol, (d) from about 8 to about 20% by weight tetraglycerol, (e) from about 3 to 10% by weight pentaglycerol and, (f) the remainder oligoglycerol.

3. A method of making an improved cosmetic or pharmaceutical preparation which comprises adding an emulsifying-effective amount of a polyglycerol polyricinoleate of claim 1 to a cosmetic or pharmaceutical preparation.

* * * * *